(12) United States Patent
Oeltgen et al.

(10) Patent No.: US 7,335,642 B2
(45) Date of Patent: *Feb. 26, 2008

(54) METHOD FOR TREATING A VIRAL INFECTION RELATED OR A CHEMICAL TOXIN RELATED HEPATIC INJURY WITH DELTORPHIN D

(75) Inventors: Peter R. Oeltgen, Winchester, KY (US); Paul D. Bishop, Fall City, WA (US); Craig J. McClain, Lexington, KY (US); Shirish Barve, Lexington, KY (US)

(73) Assignee: University of Kentucky Research Foundation, Lexington, NY (US)

(*) Notice: Subject to any disclaimer, the term of this patent is extended or adjusted under 35 U.S.C. 154(b) by 59 days.

This patent is subject to a terminal disclaimer.

(21) Appl. No.: 11/085,919

(22) Filed: Mar. 22, 2005

(65) Prior Publication Data

US 2005/0164942 A1    Jul. 28, 2005

Related U.S. Application Data

(62) Division of application No. 09/971,902, filed on Oct. 5, 2001, now Pat. No. 6,875,742.

(60) Provisional application No. 60/238,991, filed on Oct. 10, 2000.

(51) Int. Cl.
*A61K 38/10* (2006.01)
*C07K 14/435* (2006.01)

(52) U.S. Cl. .................. 514/13; 514/2; 514/893; 514/894; 514/937; 530/300; 530/302

(58) Field of Classification Search ............... None
See application file for complete search history.

(56) References Cited

U.S. PATENT DOCUMENTS

| 5,656,420 | A |   | 8/1997 | Chien    | 435/1.2 |
|-----------|---|---|--------|----------|---------|
| 6,103,722 | A |   | 8/2000 | Schultz et al. | 514/249 |
| 6,380,164 | B1|   | 4/2002 | Oeltgen et al. | 514/16 |
| 6,875,742 | B2| * | 4/2005 | Oeltgen et al. | 514/13 |

FOREIGN PATENT DOCUMENTS

WO     WO99/56766    11/1999

OTHER PUBLICATIONS

Lazarus, LH, et al., Environmental Health Perspectives, 102, 648-654, 1994.*
Cox, NJ, et al., Lancet, 354, 1277-1282, 1999.*
Okamoto, H, et al., Intervirology, 42, 196-204, 1999.*
Draganov, P, et al, Postgrad. Med., 107, 189-205, 2000, Abstract.*
elSisi, AE, et al., Toxicol. Appl. Pharmacol., 119, 280-288, 1993, Abstract.*
Barra et al., *Deltorphin, a 17 amino acid opioid peptide from the sking of the Brazilian hylid frog, Phyllomedusa burmeisteri*, Peptides (Tarrytown), vol. 15, No. 2, 1994, 199-202.
Bohlinger et al., *Interleukin-1 and nitric oxide protect against tumor necrosis factor α-induced liver injury through distinct pathways*, Hepatology, 22: 1829-1837, 1995.
Bolling et al., *Delta opioid agonist/antagonist activity and ischemic tolerance*, American Heart Association Meeting, Atlanta, GA, Nov. 1999.
Bolling et al., *The use of hibernation induction triggers for cardiac transplant preservation*, Transplantation 63: 326-329, 1997.
Bolling et al., *Use of "natural" hibernation induction triggers for myocardial protection*, Annals Thorac. Surg.: 623-627, 1997.
Bolling et al., *Hibernation triggers and myocardial protection*, Circulation 98: II220-II1224, 1998.
Chien et al., *Two-day preservation of major organs with autoperfusion multiorgan preparation and hibernation induction trigger*, J. Thorac. Cardiovasc. Surg., 102: 224-234, 1991.
Chien et al., *Extension of tissue survival time in multiorgan block preparation with a delta opioid DADLE ([D-Ala2, D-Leu5]-enkephalin)*, J. Thorac. Cardiovasc. Surg., 107: 965-967, 1994.
Crain and Shen, *Antagonists of excitatory opiod receptor functions enhance morphine's analgesic potency and attenuate opioid tolerance/dependence liability*, Pain 84 (2000), 121-131.
Fryer et al., *Opioid-induced second window of cardioprotection: Potential role of mitochondrial K-ATP channels*, Circ Res. 1999; 84: 846-851.
House et al., *A comparative study of immunomodulation produced by in vitro exposure to delta opioid receptor agonist peptides*, Peptides, (1996) 17 (1): 75-81.
Kevelaitis et al., *Opening of potassuim channels: The common cardioprotective link between perconditioning and natural hibernation?*, Circulation 99: 3079-3085, 1999.
Leist et al., *Murine hepatocyte apoptosis induced in vitro and in vivo by TNF-α requires transcriptional arrest*, The Journal of Immunology, 153: 1778-1788, 1994.
Leist et al., *Activation of the 55 kDA TNF receptor is necessary and sufficient for TNF-induced liver failure, hepatocyte apoptosis, and nitrite release*, The Journal of Immunology 154: 1307-1316, 1995.
Lishmanov et al., *Activation of the μ-opioid receptors as a factor increasing heart resistance aganist ischemic and reperfusion damages*, Russian J. Physiol. 1998; 84 (11) (Russian w/ attached English translation).
Malaguamera et al., *Elevation of interleukin 6 levels in patients with chronic hepatitis due to hepatitis C virus*, Journal of Gastroenterology, 32: 211-215, 1997.

(Continued)

Primary Examiner—Lorraine Spector
Assistant Examiner—Elly-Gerald Stoica
(74) Attorney, Agent, or Firm—Stites & Harbison PLLC; Richard S. Myers, Jr.; James Daly, IV

(57) ABSTRACT

A method of modulating cytokine mediated hepatic injury by administering compound-D SEQ ID NO:1 to a mammal. A concentration of the compound in the range of about 0.5 mg/kg to about 20 mg/kg in a physiologically acceptable formulation blocks a cytokine cascade. A therapeutic method of modulating cytokine mediated acute inflammatory, trauma induced and toxin induced hepatic injury, particularly via tumor necrosis factor modulation, is thus disclosed.

11 Claims, No Drawings

OTHER PUBLICATIONS

Maslov and Lishmanov, *Effects of μ- and delta opioid receptor ligands on rhythm and contractility disorders of isolated rat heart in postischemic period*, Kardiologya 1998; 12: 25-30 (Russian w/ English translation).

Mayfield and D'Alecy, *Delta-1 opioid receptor dependence of acute hypoxic adaptation*, J. Pharmacol. Exp. Ther. 268: 74-77, 1994.

Morgan, *Regulation of human B lymphocyte activation by opioid peptide hormones: Inhibition of IgG production by opioid receptor class (gamma-kappa-, and delta) selective agonists*, Journal of Neuroimmunology, vol. 65, No. 1: 21-30, 1996.

Oeltgen et al, *The use of delta-2 opioid agonists for myocardial ischemia protection*, Abstract, Experimental Biology 2000, submitted Nov. 1999.

Oeltgen et al., *Extended lung preservation with the use of hibernation trigger factors*, Ann. Thorac. Surg. 61: 1488-93, 1996.

Reisine et al., *Opioid analgesics and antagonists*, Goodman and Gilman's: The Pharmacological Basis of Therapeutics, 9th Ed., 1995, Section III Drugs Acting on the Central Nervous System, 23: 521-554.

Root et al., *Septicemia and septic shock*, Part Five of Infectious Diseases, Section 3, Clinical Syndromes, Harrison's Principles of Internal Medicine, 12th Ed., McGraw-Hill, 1991, 502-507.

Schultz et al., *Ischemic preconditioning in the intact rat heart is mediated by ö 1- but not μ or x-opioid receptors*, Circ 97: 1282-1289, 1998.

Schultz et al., *Morphine mimics the cardioprotective effect of ischemic preconditioning via a glibenclamide-sensitive mechanism in the rat heart*, Circ. Research. 78: 1100-1104, 1996.

Schultz et al., *Evidence for involvement of opiod receptors in ischemic preconditioning in rat hearts*, Am. J. Physiol. 268 (Heart Cir. Physiol. 3): H2157-H2161, 1995.

Schulz et al., *Involvement of activation of ATP-dependent potassium channels in ischemiec preconditioning in swine*, Am. J. Physiol. 267: H1341-1352, 1994.

Schwartz et al., *Delta opioid receptors and low temperature myocardial protection*, Ann. Thorac. Surg. 68: 2089-92, 1999.

Stefano et al., *Delta-2 opioid receptor subtype on human vascular endothelium uncouples morphione stimulated nitric oxide release*, International J. Cardiology 64: Suppl. 1, S43-S51, 1998.

Thomas et al., *Structure-sctivity relationships of a series of D-Ala2-deltorphin I and II analogues: In vitro blood-brain barrier permeability and stability*, Journal of Pharmacolopgy and Experiential Therapy, vol. 281, No. 2: 817-825, 1997.

Thornton, Jr. et al., *Opioid peptides and primary biliary cirrhosis*, BMJ, vol. 297, No. 6662: 1501-4, 1988.

Toombs et al., *Limitation of infarct size in the rabbit by ischaemic preconditioning is reversible with glibenclamide*, Cardio. Res. 27: 617-622, 1993.

Tsutsui et al., *IL-18 accounts for both TNF-α- and fas ligand-mediated hepatotoxic pathways in endotoxin-induced liver injury in mice*, The Journal of Immunology, 159: 3961-3967, 1997.

VanWinkle et al., *Cardioprotection provided by adenosine receptor activation is abolished by blockade of the K-ATP channel*, Am. J. Physiol. 266: H829-H839, 1994.

Wu et al., *Delta opioid extends hypothermic preservation time of the lung*, J. Thorac. Cardiovasc. Surg. 1996; 111: 259-267.

Zhao and Bhargava, *Effects of multiple intracerebroevntricular injections of [D-Pen2, D-Pen5] enkephalin and [D-Ala2, Glu4] deltorphin II on tolerance to their analgesic action and on brain ö-opiod receptors*, Brain Research: 745 (1997) 243-247.

\* cited by examiner

METHOD FOR TREATING A VIRAL INFECTION RELATED OR A CHEMICAL TOXIN RELATED HEPATIC INJURY WITH DELTORPHIN D

This application is a divisional of U.S. application Ser. No. 09/971,902, filed Oct. 5, 2001 now U.S. Pat. No. 6,875,742, which claims the benefit of U.S. application Ser. No. 60/238,991, filed Oct. 10, 2000, the disclosures of which are hereby incorporated by reference herein in their entirety.

FIELD OF THE INVENTION

The invention relates to the use of compounds to attenuate or prevent cytokine mediated hepatic injury.

BACKGROUND

Hepatic injury can be caused by a number of different agents including viruses such as Hepatitis A, B, C, D and E, both gram positive and gram negative bacteria, chemical agents such as ethanol, carbon tetrachloride and lead, and by physical trauma resulting in ischemia (ischemic hepatitis) injuries as can occur in right-sided congestive heart failure. It is now believed that all of these types of hepatic injury are caused at least in part by the liver's inflammatory or cytokine response to these agents. The inflammatory response of the liver results in the overexpression of a cascade of inflammatory/acute phase cytokines, such as interleukin-1 (IL-1), tumor necrosis factor (TNF), IL-6, IL-8 and transforming growth factor beta (TGFβ). It is now believed that it is the cascade of these cytokines which is the ultimate cause of much of the hepatic injury resulting from these agents. Thus, there is a need for a therapeutic agent which can be useful in alleviating or modulating the inflammatory response associated with liver disease or injury.

SUMMARY OF THE INVENTION

The present invention fills this need by providing a method of treating or preventing a cytokine mediated hepatic injury in a mammal comprised of administering a pharmaceutically effective amount of a peptide having the sequence Tyr-D-Leu-Phe-Ala-Asp-Val-Ala-Ser-Thr-Ile-Gly-Asp-Phe-Phe-His-Ser-Ile-NH$_2$ SEQ ID NO: 1, hereinafter referred to as compound D, to said mammal. The hepatic injury can be an acute inflammatory reaction, as a result of a viral or bacterial infection or a chemical agent such as ethanol, lead, carbon tetrachloride or acetaminophen, or from trauma resulting in ischemia or reperfusion injury in the liver.

The present invention is also directed to a method of treating a viral or bacterial infection-related hepatic damage in a mammal comprised of administering a pharmaceutically effective amount of compound D SEQ ID NO: 1 to said mammal.

The present invention is also directed to a method of treating alcohol induced liver injury in a mammal comprised of administering a pharmaceutically effective amount of compound D SEQ ID NO: 1 to said mammal.

Preferably, compound D SEQ ID NO:1 is administered in a pharmaceutical composition at a dosage of from about 0.5 mg/kg to about 20 mg/kg per body weight of the mammal.

Preferably, the mammal is a human.

DETAILED DESCRIPTION

A compound used to treat cytokine-mediated hepatic injury is a peptide having the sequence Tyr-D-Leu-Phe-Ala-Asp-Val-Ala-Ser-Thr-Ile-Gly-Asp-Phe-Phe-His-Ser-Ile-NH$_2$ SEQ ID NO:1, hereinafter referred to compound-D. The peptide may be produced by a number of methods, such as using an automated peptide synthesizer, through recombinant molecular techniques, or isolated from a naturally occurring source, as is known to one skilled in the art. Compound-D SEQ ID NO:1 has a molecular weight of 1,902 daltons. Compound-D SEQ ID NO:1 is insoluble in water or saline, but may be solubilized by adding 100 µM of a solution comprised of ethanol, propylene glycol, and 1 N NaOH in a 1:1:1 ratio, with sterile physiological saline then used to obtain the appropriate concentration. The initial alkaline pH is adjusted to 7.4 with 1 N HCl.

Compound-D SEQ ID NO:1 that has been solubilized may be administered by parenteral means, for example, by intravenous injection. For administration into a mammal, a dose of about 1-20 milligrams per kilogram (mg/kg) is useful. For administration into a tissue or organ preservation solution, a concentration of about 100 µM is useful.

Compound-D SEQ ID NO:1 may be administered directly into a mammal, either alone or in combination with other substances.

The above agent is administered to a mammal to modulate cytokine activation by blocking one or more steps in the cytokine cascade. The agent may be formulated for administration in an aqueous based liquid such as phosphate buffered saline to form an emulsion, or may be formulated in an organic liquid such as dimethylsulfoxide to form a solution. The solution or emulsion may be administered by any route, but it is preferably administered parenterally such as by intravenous, intramuscular, intradermal or intraperitoneal injections. A preferred dose is in the range of about 0.5-20 mg of compound-D SEQ ID NO:1 per kg of body weight of the mammal. The time of administration of the agent is preferably prior to initiation of cytokine activation. However, the agent may be administered concurrently with another agent that induces cytokine activation or even subsequent to an agent that induces cytokine activation and still produce a protective effect.

Administration of compound-D SEQ ID NO:1 should be continued on a daily basis until hepatic function returns to normal and is maintained at normal levels, preferably for at least one to two days. Hepatic injury can be determined by elevated levels of hepatic enzymes, as well as by depressed albumin levels (less than about 35 g/liter). Hepatic function is routinely monitored by quantitating serum levels of hepatic enzymes such as alanine aminotransferase (ALT) (normal<35 U/L), aspartate aminotransferase (AST) (normal<30 U/L), alkaline phosphatase (ALP) (normal≦100

U/L) and gamma glutamyltransferase (GGT) (normal≦45 U/L for males, ≦30 U/L for females), as well as bilirubin, both conjugated (normal≦0.2 mg/deciliter) and total (normal≦1.0 mg/deciliter) bilirubin. Compound-D SEQ ID NO:1 modulation of hepatocyte cytokine activation may be used therapeutically in a variety of hepatic injury processes. As used herein, the term hepatic injury broadly encompasses all types of injury such as hepatic trauma, physical and/or chemical insult, stress, inflammation, toxicity, disease and so on. For example, the inventive agents can be used in treating hepatic injury due to alcoholic liver disease, acetaminophen toxicity, cadmium toxicity, lead poisoning, bacteremia due to, for example, *Staphylococcus* species, *Streptococcus* species, *Neisseria* species, *Salmonella* species, *Shigella* species, *Escherichia coli, Clostridium perfringens, Klebsiella* species, *Proteus* species, *Enterobacter* species, *Bacteroides* species, *Brucella* species, *Francisella tularensis, Listeria monocytogenes, Acinetobacter* species, *Streptobacillus moniliformis, Vibrio* species, *Helicobacter pylori, Pseudomonas* species, *Haemophilus* species, *Bordetella pertussis*, viral infections due to, for example, influenza viruses, adenoviruses, paramyxoviruses, rubella viruses, polioviruses, hepatitis viruses, herpesviruses, rabies viruses, human immunodeficiency viruses and papilloma viruses, as well as trauma, ischemia reperfusion injury and metabolic liver disease.

While the specific mechanism of action of compound-D SEQ ID NO:1 on the modulation of cytokine mediated hepatic injury such as acute inflammatory reactions, trauma and toxin induced biological responses is unknown, these agents exhibit a specific and reproducible effect on decreasing hepatotoxicity.

A treatment for attenuating and/or preventing cytokine mediated acute inflammatory, trauma induced and toxin induced hepatic injury is thus disclosed. Compound-D SEQ ID NO:1, administered at a concentration of about 0.5 mg/kg to about 20 mg/kg, inhibits hepatic injury and result in decreased lethality of an injured animal.

It should be understood that the embodiments of the present invention shown and described in the specification are only preferred embodiments of the inventors who are skilled in the art and thus are not limiting in any way. Therefore various changes, modifications or alterations to these embodiments may be made or resorted to without departing from the spirit of the invention and the scope of the following claims.

What is claimed is:

1. A method for treating a viral infection related hepatic injury in a mammal comprising administering a pharmaceutically effective concentration of the peptide shown in SEQ ID NO:1 for a duration sufficient to treat the hepatic injury related to the viral infection.

2. The method of claim 1 wherein the viral infection is caused by a hepatitis virus.

3. The method of claim 1 wherein said compound is administered prior to said hepatic injury related to the viral infection.

4. The method of claim 1 wherein said compound is administered subsequent to said hepatic injury related to the viral infection.

5. The method of claim 1 wherein said compound is administered substantially concurrently with said hepatic injury related to the viral infection.

6. The method of claim 1 wherein said compound is administered in the formulation selected from the group consisting of a solution, an emulsion and a suspension.

7. The method of claim 1 wherein said compound is administered parenterally.

8. The method of claim 1 wherein said compound is administered at a concentration in the range of about 0.5 mg/kg to about 20 mg/kg.

9. The method of claim 1 wherein said compound is administered at least until hepatic function normalizes.

10. A method for treating chemical toxin related hepatic injury in a mammal comprising administering a pharmaceutically effective concentration of the peptide shown in SEQ ID NO:1 for a duration sufficient to treat the hepatic injury caused by the chemical toxin.

11. The method of claim 10 wherein the chemical toxin is selected from the group consisting of ethanol, lead, cadmium, carbon tetrachloride, and acetaminophen, and combinations thereof.

* * * * *

SEQUENCE LISTING

```
<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<221> NAME/KEY: MOD_RES
<222> LOCATION: (1)...(17)
<223> OTHER INFORMATION: Xaa = D-Leu; artificial sequence is completely
      synthesized

<400> SEQUENCE: 1

Tyr Xaa Phe Ala Asp Val Ala Ser Thr Ile Gly Asp Phe Phe His Ser Ile
 1               5                  10                  15
```